United States Patent
Bruchmann et al.

(10) Patent No.: US 6,913,629 B2
(45) Date of Patent: Jul. 5, 2005

(54) BUILDING BLOCKS CONTAINING ISOCYANATE GROUPS AND THEIR USE FOR FUNCTIONALIZING OR MODIFYING COMPOUNDS OR SURFACES

(75) Inventors: Bernd Bruchmann, Freinsheim (DE); Ulrich Treuling, Bensheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 99 days.

(21) Appl. No.: 09/726,045

(22) Filed: Nov. 30, 2000

(65) Prior Publication Data

US 2001/0005738 A1 Jun. 28, 2001

(30) Foreign Application Priority Data

Dec. 23, 1999 (DE) .......................................... 199 62 272

(51) Int. Cl.$^7$ ........................ D06M 13/22; C07C 69/88; C08G 18/81
(52) U.S. Cl. .................. 8/181; 8/115.51; 8/192; 560/330; 560/338; 560/65; 528/45
(58) Field of Search ...................... 8/181, 192, 115.51; 560/330, 338, 65; 528/45

(56) References Cited

U.S. PATENT DOCUMENTS

| | | | |
|---|---|---|---|
| 3,996,257 A | 12/1976 | Larsen ........................ 260/455 |
| 4,002,601 A | 1/1977 | Hajek et al. ................... 260/77 |
| 4,008,196 A | * 2/1977 | Matsuda et al. ............ 260/29.2 |
| 4,180,491 A | * 12/1979 | Kim et al. ................... 260/29.2 |
| 4,315,840 A | 2/1982 | Kempter et al. ............... 260/18 |
| 5,189,093 A | 2/1993 | Beziers et al. ................ 524/847 |
| 5,693,768 A | 12/1997 | Bachmann et al. ........... 536/4.1 |
| 5,856,416 A | 1/1999 | Bachmann et al. ............. 220/4 |
| 5,981,684 A | 11/1999 | Bruchmann et al. ........... 528/45 |
| 6,080,831 A | * 6/2000 | Jansen et al. .................. 528/65 |
| 6,420,508 B1 | * 7/2002 | Danielmeier et al. ......... 528/49 |

FOREIGN PATENT DOCUMENTS

| | | |
|---|---|---|
| EP | 0 124 021 | 11/1984 |
| EP | 1 026 174 | 8/2000 |
| GB | 885523 | 12/1958 |
| GB | 1 239 677 | 7/1971 |
| WO | WO 97/02304 | 1/1997 |
| WO | WO 97/36857 | 10/1997 |

OTHER PUBLICATIONS

Sinyavskii et al. "Products of the Reaction of Hexamethylene Diisocyanate with Certain Alcohols" J. Organ. Chem. of USSR No. 5 (1967) pp. 836–839.

Chen et al. "Modifications of Montmorillonite with toulene—2,4–DI–iscyanate and preparation and characterization of polystyrene/montmrillonite nanocomposite" Chemical Abstract vol. 134 abstract No. 57436 (2000).

Ghosh et al. "Molecular recognition on giant vesicles: coating of phytyl phosphate vesicles with a polysaccharide bearing phytyl chains" Chem. Commun. (2000) pp. 267–268.

Peerlings et al. "A mild and convenient method for the preparation of mult–isocyanates starting from primary amnies" Tetrahedron Letters No. 40 (1999) PP. 1021–1024.

* cited by examiner

Primary Examiner—Yogendra N. Gupta
Assistant Examiner—Preeti Kumar
(74) Attorney, Agent, or Firm—Keil & Weinkauf

(57) ABSTRACT

Compounds of the formula 1

$$\text{OCN—R}^1\text{—NHCOX—R}^2\text{—(Y)}_n \qquad (1),$$

where X is a covalent bond to $R^2$ or is O, S or $NR^3$, Y is a hydrogen atom or a free functional group and n is an integer from 1 to 20, can be used for functionalizing or modifying compounds or solid surfaces which have at least one group which is reactive toward isocyanate.

5 Claims, No Drawings

BUILDING BLOCKS CONTAINING ISOCYANATE GROUPS AND THEIR USE FOR FUNCTIONALIZING OR MODIFYING COMPOUNDS OR SURFACES

The present invention relates to compounds of the formula 1

$$OCN—R^1—NHCOX—R^2—(Y)_n \quad (1),$$

where X is a covalent bond to $R^2$ or O, S or $NR^3$ and Y is a hydrogen atom or a free functional group, a process for preparing them and their use for functionalizing or modifying compounds or surfaces which have at least one group which is reactive toward isocyanate.

An increasing number of new application areas are being developed both for conventional functionalized monomers or polymeric structures, e.g. for monomeric or polymeric bifunctional, trifunctional or higher-functional alcohols or amines, and also for macromolecular structures having a high degree of branching and/or a large number of functional groups on the periphery of the molecule (functionalized macromolecules), for example dendrimers, highly branched and hyperbranched polymers and star polymers. For certain applications, it is necessary to mask particular functional groups of the functionalized monomers or polymers or else to vary the functional groups. For example, it can be advantageous to make hydrophilic molecules hydrophobic or hydrophobic molecules hydrophilic. It can also be advantageous, for example, to convert amino groups into hydroxyl groups or carboxyl groups or to transform OH groups into activatable double bonds. Furthermore, there is a general need for the functionalization or modification of functional groups on surfaces in order to alter the properties of the surface in an appropriate way.

WO 97/36857 describes the use of OH-protected trihydroxyalkylaminoalkanes which are converted into a monoisocyanate by means of phosgenation. The resulting isocyanate building block is used to modify isocyanate-reactive groups in dendritic molecules. However, the starting materials used in this method of preparing monoisocyanates are synthetically complicated to prepare and the process can only be carried out using small quantities. Furthermore, only groups which are unreactive toward NCO groups can be initially introduced into the macromolecule. The formation of, for example, hydroxyl or carboxylic acid groups requires the additional reaction step of ether or ester cleavage. H. W. I. Peerlings and E. W. Meijer, Tetrahedron Lett. 40 (1999) 1021–1024, likewise describe the use of specially prepared alkyl monoisocyanates and aryl monoisocyanates for the surface modification of polyamine dendrimers. Here too, only groups which are unreactive toward isocyanates are introduced into the macromolecule.

Furthermore, R. M. Versteegen, R. P. Sijbesma and E. W. Meijer, Angew. Chem. 1999, 111, 3095–3097, describe the synthesis of [η]-polyurethanes in which phosgenation of linear aliphatic α,ω-aminoalcohols is used for the in-situ generation of hydroxyisocyanates which are not stable in the reaction solution and immediately polymerize to form linear polyurethanes.

There is therefore a continuing need for building blocks which make it possible to functionalize or modify compounds or surfaces having isocyanate-reactive groups in any desired way.

It is an object of the present invention to provide building blocks containing isocyanate groups which can be used for functionalizing or modifying compounds or surfaces having at least one group which is reactive toward isocyanate. A further object of the invention is to provide a process for preparing these building blocks.

We have found that this object is achieved by compounds of the formula 1

$$OCN—R^1—NHCOX—R^2—(Y)_n \quad (1),$$

as described in the following text.

The present invention provides compounds of the formula 1, hereinafter referred to as building blocks, $$OCN—R^1—NHCOX—R^2—(Y)_n \quad (1),$$

where $R^1$ and $R^2$ are each a substituted or unsubstituted, linear or branched, saturated or unsaturated alkylene radical having from 1 to 20 carbon atoms, preferably from 2 to 20 carbon atoms, more preferably from 4 to 20 carbon atoms and particularly preferably from 6 to 20 carbon atoms, a substituted or unsubstituted, saturated or unsaturated cycloalkylene radical having from 3 to 20 carbon atoms, a substituted or unsubstituted arylene radical having from 3 to 20 carbon atoms, an arylenealkylene radical having from 4 to 20 carbon atoms, a heterocyclic radical or any linear or branched sequence of two or more of the radicals mentioned, if desired linked via ether, thioether, ester, amine or amide structures, X is a covalent bond to $R^2$ or O, S or $NR^3$, here $R^3$ is a hydrogen atom or a substituted or unsubstituted, linear or branched, saturated or unsaturated alkyl radical having from 1 to 20 carbon atoms, a substituted or unsubstituted, saturated or unsaturated cycloalkyl radical having from 3 to 20 carbon atoms, a substituted or unsubstituted aryl radical having from 3 to 20 carbon atoms, a heterocyclic radical or any linear or branched sequence of two or more of the radicals mentioned, Y is a free functional group and n is an integer from 1 to 20, preferably from 1 to 5, particularly preferably from 1 to 3. Y can also be a hydrogen atom.

The invention further provides a process for functionalizing or modifying compounds or surfaces which have at least one group which is reactive toward isocyanate, by reacting a compound of the formula 1

$$OCN—R^1—NHCOX—R^2—(Y)_n \quad (1),$$

where $R^1$, $R^2$, X, Y and n are as defined above, with at least one isocyanate-reactive group of a compound having at least one isocyanate-reactive group, or with at least one isocyanate-reactive group on a surface which has at least one isocyanate-reactive group.

The invention further provides for the use of a compound of the formula 1

$$OCN—R^1—NHCOX—R^2—(Y)_n \quad (1),$$

where $R^1$, $R^2$, X, Y and n are as defined above, for functionalizing or modifying compounds or surfaces which have at least one group which is reactive toward isocyanate.

Finally, the invention provides a process for preparing a compound of the formula 1

$$OCN—R^1—NHCOX—R^2—(Y)_n \quad (1)$$

by reacting a diisocyanate of the formula 2

$$OCN—R^1—NCO \quad (2)$$

with a compound of the formula 3

$$HX—R^2—(Y)_n \quad (3),$$

where $R^1$, $R^2$, $R^3$, X, Y and n are as defined above and X in formula 3 can also be OCO.

For the purposes of the present invention, a substituted alkylene radical is an alkylene radical which is substituted at at least one place by a $C_1$–$C_6$-alkyl radical, a $C_3$–$C_8$-aryl radical, a halogen atom selected from among fluorine, chlorine, bromine or iodine, or a mixture thereof. The terms substituted cycloalkylene radical, substituted arylene radical, substituted alkyl radical, substituted cycloalkyl radical and substituted aryl radical are defined analogously.

For the purposes of the present invention, a free functional group is a reactive position which is not protected by a protective group. Examples of free functional groups which can be used for the purposes of the present invention are hydroxyl, thiol, nitro, substituted or unsubstituted amino, amido, sulfonic acid, sulfenic acid, sulfinic acid, sulfonamide, carbonyl, carboxyl, nitrile, isonitrile, cyanate, isocyanate, thiocyanate, isothiocyanate, silyl, silanyl, substituted or unsubstituted phosphine, phosphoric acid, phosphorous acid, phosphonate, acryl, methacryl, vinyl, allyl and acetylene groups and halogen atoms.

In the formulae, Y is preferably a vinyl, allyl, sulfonyl, sulfenyl, sulfinyl, sulfonamide, carbonyl, silyl, silanyl, hydroxy, thiol, carboxyl, sulfonic acid, acryl, methacryl or substituted or unsubstituted amino group.

Y is particularly preferably a hydroxy, thiol, carboxyl, sulfonic acid, acryl, methacryl or substituted or unsubstituted amino group.

For the purposes of the present invention, a substituted amino group is an amino group which is substituted by one or two substituents selected from the group consisting of $C_1$–$C_6$-alkyl radicals, $C_3$–$C_8$-aryl radicals, halogen atoms selected from among fluorine, chlorine, bromine and iodine, and mixtures thereof.

For the purposes of the present invention, a group which is reactive toward isocyanate (also referred to as an isocyanate-reactive group) is a group which bears hydrogen atoms which are reactive toward NCO groups or which can form an addition compound with NCO groups. Examples of such groups are OH, SH, NH, COOH groups, epoxides, acid anhydride or carbodiimide groups; among these, preference is given to OH, SH, NH or COOH groups.

In a preferred embodiment of the building blocks of the present invention, $R^1$ is a 2,4-tolylene, 2,6-tolylene, 4,4'-diphenylmethylene, 2,4'-diphenylmethylene, 3-alkyl-4,4'-diphenylmethylene, where alkyl is $C_1$–$C_{10}$-alkyl, 1,3- and 1,4-phenylene, 1,5-naphthylene, tolidine, biphenylene, tetramethylene, hexamethylene, dodecylene, alkylene lysine ester where alkylene is $C_1$–$C_{10}$-alkylene, isophoronylene, 2-methylpentamethylene, 2,2,4- and 2,4,4-trimethyl-1,6-hexamethylene, 1,4-cyclohexylene, 3-methylene-1-methyl-1-cyclohexylene, 2-butyl-2-ethylpentamethylene, 4-methyl-1,3-cyclohexylene, 4,4'- and 2,4'-methylenebis(cyclohexylene), xylylene, tetramethylxylylene radical or a mixture thereof and $R^2$ is a linear or branched, saturated or unsaturated alkylene or cycloalkylene radical having from 1 to 20 carbon atoms, a substituted or unsubstituted arylene radical having from 3 to 20 carbon atoms or any linear or branched sequence of two or more of the radicals mentioned which may, if desired, be linked to one another via ether, thioether, amine, amide or ester groups. Mixtures of the specified radicals $R^2$ are also possible.

To prepare the building blocks of the present invention, diisocyanates are reacted with alcohols, thiols, primary or secondary amines or carboxylic acids to form the corresponding addition products. In the case of the reaction with carboxylic acids, this generally proceeds with elimination of $CO_2$. Particular preference is given to the reaction of diisocyanates with alcohols, thio alcohols and amines.

The reaction is generally carried out at from 0 to 120° C. and the reaction time is usually from 5 minutes to 24 hours. The reaction is preferably carried out under protective gas with or without a solvent, if desired with addition of catalysts customary in polyurethane chemistry. Preference is given to using solvents which are inert toward isocyanate groups. Examples which may be mentioned are benzene, toluene, chlorobenzene, dichlorobenzene, diethyl ether, tetrahydrofuran, dioxane, acetone, 2-butanone, ethyl acetate, butyl acetate, chloroform, methylene chloride, N-methylpyrrolidone, dimethylformamide and dimethylacetamide.

In a preferred embodiment, diisocyanates whose isocyanate groups have differing reactivity toward the component which is reactive toward isocyanate are used as starting materials. In this case, the building blocks of the present invention are obtained by reacting equimolar amounts of this diisocyanate with the isocyanate-reactive compound of the formula 3. As a result of the reactivity difference between the NCO groups, the selectivity is generally high enough for the desired monoadducts to be formed in appropriate purity.

In a further embodiment, isocyanates having NCO groups of equal reactivity are used. These are usually reacted in a 2- to 15-fold, preferably 5- to 10-fold, molar excess with the NCO-reactive compound of the formula 3, and the excess isocyanate is subsequently removed.

As isocyanates for preparing the building blocks of the present invention, it is in principle possible to use all organic diisocyanates. Preference is given to using tolylene 2,4-diisocyanate, tolylene 2,6-diisocyanate, diphenylmethane 4,4'-diisocyanate, diphenylmethane 2,4'-diisocyanate, 3-alkyldiphenylmethane 4,4'-diisocyanate, where alkyl is $C_1$–$C_{10}$-alkyl, phenylene 1,3- and 1,4-diisocyanate, naphthylene 1,5-diisocyanate, tolidine diisocyanate, biphenyl diisocyanate, tetramethylene diisocyanate, hexamethylene diisocyanate, dodecylene diisocyanate, lysine alkyl ester diisocyanate, where alkyl is $C_1$–$C_{10}$-alkyl, isophorone diisocyanate, 2-methylpentamethylene diisocyanate, 2,2,4- or 2,4,4-trimethylhexamethylene 1,6-diisocyanate, 1,4-diisocyanatocyclohexane, 3-isocyanatomethyl-1-methyl-1-isocyanatocyclohexane, 2-butyl-2-ethylpentamethylene diisocyanate, 2-isocyanatopropylcyclohexyl isocyanate, 4-methylcyclohexane 1,3-diisocyanate, dicyclohexylmethane 4,4'- and 2,4'-diisocyanate, 1,3- or 1,4-bis(isocyanatomethyl)cyclohexane, xylylene diisocyanate and tetramethylxylylene diisocyanate (TMXDI).

Particular preference is given to isocyanates having NCO groups of differing reactivity, e.g. aromatic diisocyanates such as tolylene 2,4-diisocyanate (2,4-TDI), diphenylmethane 2,4'-diisocyanate (2,4'-MDI), 3-alkyldiphenylmethane 4,4'-diisocyanate, where the alkyl radical has from 1 to 10 carbon atoms, or aliphatic diisocyanates such as isophorone diisocyanate (IPDI), 2-butyl-2-ethylpentamethylene diisocyanate, 2-isocyanatopropylcyclohexyl isocyanate, 3-isocyanatomethyl-1-methyl-1-isocyanatocyclohexane, lysine alkyl ester diisocyanate, where alkyl is $C_1$–$C_{10}$-alkyl, dicyclohexylmethane 2,4'-diisocyanate (2,4'-HMDI) and 4-methylcyclohexane 1,3-diisocyanate (H-TDI).

Furthermore, particular preference is given to isocyanates whose NCO groups initially have equal reactivity, but in which addition of an alcohol or amine onto one NCO group is able to induce a decrease in the reactivity of the second NCO groups. Examples are isocyanates whose NCO groups are coupled via an electronic system, e.g. phenylene 1,3- and 1,4-diisocyanate, naphthylene 1,5-diisocyanate (NDI), biphenyl diisocyanate, tolidine diisocyanate and tolylene 2,6-diisocyanate (2,6-TDI).

Particular preference is also given to isocyanates whose NCO groups have equal reactivity but can easily be removed from the reaction mixture by distillation, e.g. tetramethylene diisocyanate, hexamethylene diisocyanate, 1,3- and 1,4-bis (isocyanatomethyl)cyclohexane, tetramethylxylylene diisocyanate, xylylene diisocyanate, diphenylmethane 4,4'-diisocyanate or dicyclohexylmethane 4,4'-diisocyanate.

Mixtures of the isocyanates mentioned can also be used for preparing the building blocks of the present invention.

The process of the present invention makes it possible to produce and isolate structures which contain both isocyanate groups and groups which are reactive toward isocyanate. Thus, for example, the reaction product of tetramethylxylylene diisocyanate (TMXDI) and diisopropanolamine has one NCO group and two secondary OH groups. It can be isolated as a solid and can be stored for some time (about 24 hours) at room temperature.

Examples of preferred building blocks of the present invention are addition products of hexamethylene diisocyanate, isophorone diisocyanate, tetramethylxylylene diisocyanate, tolylene 2,4'-diisocyanate, diphenylmethane 4,4'-diisocyanate, diphenylmethane 2,4'-diisocyanate or p-phenylene diisocyanate and monoalcohols, for example methanol, ethanol, propanol, butanol, hexanol, hexenol, octanol, decanol, dodecanol, octadecanol, octadecenol, allyl alcohol or benzyl alcohol, etherified monoalcohols such as ethylene glycol monomethyl ether, propylene glycol monomethyl ether, polyethylene glycol monomethyl ether or polypropylene glycol monomethyl ether, thio alcohols such as mercaptoethanol, butanethiol or dodecanethiol, monoamines such as methylamine, ethylamine, propylamine, butylamine, dibutylamine, hexylamine, octylamine, decylamine, aniline or benzylamine, polyalkylene oxides functionalized with amino groups, monocarboxylic acids such as acetic acid, propionic acid, butyric acid, hexanoic acid, octanoic acid, decanoic acid or benzoic acid, dialkanolamines such as diethanolamine, dipropanolamine or diisopropanolamine, trialkanolamines such as tris (hydroxymethyl)aminomethane or tris(hydroxyethyl) aminomethane, hydroxycarboxylic acids such as hydroxyacetic acid, hydroxypropionic acid or hydroxypivalic acid, mercaptocarboxylic acids such as mercaptoacetic acid or mercaptopropionic acid, aminocarboxylic acids such as glycine, β-alanine or aminocaproic acid, or aminosulfonic acids such as taurine. If the acids are used in the form of their salts, preference is given to sodium, potassium or ammonium salts. Further possible building blocks are phosphorus-containing compounds such as (2-hydroxyalkyl) triphenylphosphonium salts, 1-(diphenylphosphinoyl) propan-2-ol, aminoethyldiphenylphosphine or silicon-containing compounds such as trimethylsilylmethanol, trimethylsilylethanol, dimethylphenylsilylmethanol, hydroxymethyltriethoxysilane, 3-aminopropyltrimethoxysilane or 3-aminopropyltriethoxysilane. Further suitable building blocks are hydroxy acrylates such as hydroxyethyl acrylate, hydroxypropyl acrylate, hydroxybutyl acrylate, hydroxyethyl acrylate and hydroxyalkylacrylamides such as hydroxymethylacrylamide or hydroxymethylmethacrylamide.

If a building block of the present invention is used for functionalizing a compound or a surface which has groups which are reactive toward isocyanate, it is advantageous but not absolutely necessary to generate this building block in situ and subsequently to react it with the compound or surface having groups which are reactive toward isocyanate. The choice of the isocyanate and the molecular fragment —(Y)$_n$ of the isocyanate-reactive compound of the formula 3 is made according to the properties which the compound or surface having isocyanate-reactive groups is to have after functionalization or modification with the building blocks.

The functionalization or modification of a compound or a surface is carried out by bringing the NCO-containing building blocks of the present invention, either in pure form or in a solvent, into contact with the compound or surface to be functionalized or modified. The reaction between the NCO groups of the building blocks of the present invention and the NCO-reactive groups of the compound or surface to be functionalized or modified preferably takes place at from 0 to 120° C. for reaction times of from 5 minutes to 24 hours, if desired with addition of catalysts. Here, the building blocks of the present invention can also be used in a substoichiometric amount, based on the functional groups of the substrate to be functionalized or modified, in order to carry out, if desired, a partial modification of the compound or the surface.

In a preferred embodiment of the present invention, the compound having isocyanate-reactive groups is a monomer or a polymer bearing functional groups, preferably as end groups or as side groups, which are reactive toward isocyanate. Examples of monomers are OH- or NH-containing substances such as ethylene glycol, propylene glycol, butanediol, pentanediol, hexanediol, glycerol, trimethylolpropane, pentaerythritol, sorbitol, sugar, ethylenediamine, butylenediamine, hexylenediamine or melamine. Examples of polymers are OH-containing polymers such as polyether polyols, polyester polyols, polyacrylate polyols, polyvinyl alcohols, polybutadiene alcohols, NH-containing polymers such as amino-terminated polyetherols, polyalkylenimines, polyalkyleneamines, polyvinylimidazoles, polyamidoamines and polymers containing acid or acid anhydride groups, e.g. polyacrylic acids or polymers containing maleic anhydride groups.

Preference is given to polymers containing OH or NH groups, for example polyetherols, polyesterols, polyacrylate polyols, polyethylenimines or polyvinylamines.

In a further embodiment of the present invention, the compound which has groups which are reactive toward isocyanates is a dendrimer, a highly branched or hyperbranched polymer or a star polymer, in each case having the periphery of the molecule functionalized by, for example, hydroxy, amino, carboxy, thiol or NCO-reactive silane groups.

For the purposes of the present invention, dendrimers are macromolecules which are structurally and molecularly uniform and have branched molecular chains going out from a central molecule. For the purposes of the present invention, a highly branched or hyperbranched polymer is a polymer formed by intermolecular polymerization of molecules of the AB$_n$ type, where A and B can react with one another and n is preferably from 1 to 3. Like dendrimers, these molecules have a high degree of branching but are structurally non-uniform and have a molar mass distribution.

A star polymer may be regarded as a special case of a dendritic or highly branched or hyperbranched structure. They have a single central molecule or an oligomer having a low degree of branching as nucleus to which polymeric chains which are preferably linear or slightly branched are attached in the form of a star.

A more detailed description of the structures mentioned may be found, for example, in E. Malmström and A. Hult, J. M. S.-Rev. Macromol. Chem. Phys., 1997, C 37(3), 555–579, "Dendritic Molecules", G. R. Newkome, C. N. Moorefield, F. Vögtle, Verlag Chemie, Weinheim 1996 and "Topics in Current Chemistry No. 197, Dendrimers", F. Vögtle, Springer-Verlag, Berlin-Heidelberg, 1998 and J. Huybrechts and K. Dusek, Surface Coatings International 1998, 3, 117–127.

In a further embodiment, the building blocks of the present invention can be used to functionalize or modify various surfaces which have groups which are reactive toward isocyanate. Here, the properties which the surface having isocyanate-reactive groups is to have after the functionalization or modification with the building blocks are achieved by selection of the isocyanate and the molecular fragment —$(Y)_n$ of the isocyanate-reactive compound of the formula 3. The surfaces used in the present invention can, for example, be selected from among (the respective isocyanate-reactive groups are indicated in brackets):
glass (OH), wood (OH), textiles, for example of cotton (OH) or wool (OH, NH, SH, COOH), leather (OH, NH, SH, COOH), paper (OH), plastic (OH, NH, SH, COOH), ceramic (OH), masonry (OH), concrete (OH) or partially oxidized metals (OH).

Preferred surfaces are glass, wood, paper and textiles.

The invention is illustrated by the examples below.

EXAMPLES

1. Preparation of NCO-containing Monourethanes and Monoureas 1.1. Monourethanes Derived from Hexamethylene Diisocyanate (HDI)

1680 g of HDI (10 mol) and 0.84 g of dibutyltin dilaurate (500 ppm based on HDI) were placed in a reaction vessel under a blanket of nitrogen and heated to 60° C. At this temperature, 2 mol of the respective alcohol as shown in Table 1 were added dropwise over a period of 30 minutes. The mixture was allowed to react for another 30 minutes at 60° C. The product was subsequently freed of monomeric HDI by distillation under reduced pressure in a thin film evaporator. The data for the products 1 to 3 are shown in Table 1.

1.2. Monourethane Derived from Tolylene 2,4-diisocyanate (TDI)

The aromatic diisocyanate was dissolved in dry chlorobenzene under a blanket of nitrogen, the mixture was heated to 80° C. and the OH component indicated in Table 1 was added dropwise at this temperature over a period of 30 minutes. The mixture was subsequently allowed to react for another 60 minutes at 80° C. The molar ratio of isocyanate to the alcohol was 1:1. Apart from unreacted diisocyanate, the diadduct was formed as by-product, but this could, if desired, be removed by purification operations (chromatography, crystallization). The data for product 4 are shown in Table 1.

TABLE 1

OH-components as reactants

| Product No. | Isocyanate | Alcohol | NCO content (% by wt.) | Properties |
|---|---|---|---|---|
| 1 | HDI | Octadecanol | 9.6 | Melting point: 57–58° C. |
| 2 | HDI | cis-9-Octadecen-1-ol | 9.6 | Melting point: 28–31° C. |
| 3 | HDI | Hydroxyethyl methacrylate | 14.1 | Viscosity at 23° C., 80% in ethyl acetate: 77 mPas |
| 4 | TDI | Hydroxyethyl acrylate | 14.5 | Melting point: 38–40° C. |

HDI = Hexamethylene 1,6-diisocyanate
TDI = Tolylene 2,4-diisocyanate 1.3. Monothiourethane Derived from Isophorone Diisocyanate (IPDI)

222 g of IPDI (1 mol) were placed in a reaction vessel under a blanket of nitrogen and heated to 50° C. At this temperature, 1 mol of mercaptoacetic acid dissolved in 200 ml of dry chlorobenzene as added dropwise over a period of 30 minutes. The mixture was allowed to react for another 60 minutes at 50° C. The addition product was preferably not purified or isolated, but reacted directly with the molecules or surfaces to be modified or functionalized. The data for the product 5 are shown in Table 2.

1.4. Monoureas Derived from Diisocyanates and Amines or Alkanolamines 1 mol of the respective isocyanate was dissolved in 300 ml of THF (dry) and cooled to 10° C. 1 mol of the appropriate amine dissolved in 100 ml of THF was subsequently added over a period of 30 minutes, with the temperature being maintained at 10° C. The mixture was stirred for another 30 minutes at 10° C. The products from TMXDI were found to be surprisingly stable and could be stored for some time (about 24 hours) at room temperature without polymerization. The adducts derived from IPDI were preferably not isolated, but reacted directly with the molecules or surfaces to be modified or functionalized. Data for the products 6 to 11 according to the present invention are shown in Table 2.

TABLE 2

Components containing SH and COOH groups or NH and OH groups as reactants

| Product No. | Isocyanate | Reactive component | NCO content (% by wt.) | Purity (% by area in GPC) |
|---|---|---|---|---|
| 5 | IPDI | Mercaptoacetic acid | 13.4 | 90.0 |
| 6 | IPDI | Dodecylamine | 10.3 | 99.0 |
| 7 | IPDI | Isopropanolamine | 14.1 | 91.0 |
| 8 | IPDI | Diisopropanolamine | 11.8 | 99.0 |
| 9 | TMXDI | Diethanolamine | 12.0 | 89.0 |
| 10 | TMXDI | Diisopropanolamine | 11.1 | 96.0 |
| 11 | TMXDI | Tris (hydroxymethyl)-aminomethane | 11.5 | 91.0 |

IPDI = Isophorone diisocyanate
TMXDI = Tetramethylxylylene diisocyanate

2. Modification of Macromolecules 2.1. Modification of a Polyamine Dendrimer Having $NH_2$ Functionality 8 as Described in WO 93/14147, Commercially Available as ASTRAMOL® Grade from DSM N.V.

The reaction product of HDI and octadecenol (monourethane 2 from Table 1) and dry THF were placed in a reaction vessel and cooled to 10° C. At this temperature, the dendritic polyamine (M=773 g/mol) dissolved in THF was added over a period of 30 minutes, and the mixture was subsequently stirred at 23° C. for another 1 hour. The amount added was calculated so that 1 mol of $NH_2$ groups of the polyamine per mol of NCO groups was reacted. The product which precipitated was filtered off, washed with THF and dried under reduced pressure at 40° C. Yield: 93% of theory, melting point 119–120° C.

While the polyamine dendrimer dissolved, for example, in water or ethanol, the modified product was not soluble in these. However, the modified dendrimer dissolved in, for example, chlorobenzene, n-heptane or isooctane.

2.2. Modification of a Polyethylenimine 118 g of the reaction product of HDI and octadecenol (monourethane 2 from Table 1) and 400 ml of dry THF were placed in a reaction vessel. At room temperature (23° C.), 10.5 g of polyethylenimine ($M_n$=700 g/mol) dissolved in 100 ml of distilled water were added over a period of 30 minutes, and this mixture was subsequently stirred at 23° C. for another 4 hours. The reaction mixture was admixed with 2 l of acetone, stirred well and allowed to stand for 12 hours. The solid which precipitated was filtered off, washed with acetone and dried under reduced pressure at 40° C.

The yield was 89% of theory and the melting point was 119–121° C.

While the polyethylenimine dissolved in water, the modified product was insoluble therein. However, it did dissolve in, for example, chlorobenzene or butyl acetate.

2.3. Functionalization of a High-functionality Polyacrylate Alcohol (Lumitol® H 136, BASF AG)

25 g of the adduct of TDI and hydroxyethyl acrylate (monourethane 4 from Table 1) was dissolved in 100 ml of dry chlorobenzene and heated to 40° C. A solution of 68.7 g of Lumitol® H 136 in 100 ml of butyl acetate was added dropwise over a period of 1 hour and the mixture was subsequently stirred at 40° C. for 4 hours. After this time, IR spectroscopy no longer detected any NCO bands in the product mixture. Taking off the solvent gave a solid which contained acrylate groups and had a melting range of 31–35° C.

3. Modification of Surfaces: Hydrophobicization of a Woven Cotton Fabric

Two solutions (solution 1 and solution 2) comprising 100 ml of dry tetrahydrofuran and 50 mg of dibutyltin dilaurate were prepared in parallel. 2 g of the adduct of HDI and octadecenol (monourethane 2 from Table 1) were additionally added to solution 1 and dissolved therein. A 5×10 cm piece of a woven cotton fabric was subsequently placed in each of the two solutions and the reaction solutions together with the fabric pieces were heated in parallel at 60° C. for 2 hours. After cooling, the woven cotton fabrics were taken from the solutions, each washed with 2×100 ml of tetrahydrofuran and dried completely by means of a hot air blower. The fabrics were subsequently wetted with water. While the untreated fabric from solution 2 became fully soaked by the water, the water all ran off in beads from the monourethane-modified fabric.

We claim:

1. A process for functionalizing or modifying compounds or surfaces having at least one group which is reactive toward isocyanate, by reacting a compound of the formula 1

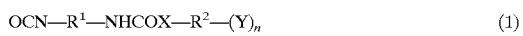

$$OCN-R^1-NHCOX-R^2-(Y)_n \quad (1)$$

where $R^1$ and $R^2$ are each a substituted or unsubstituted, linear or branched saturated or unsaturated alkylene radical having from 1 to 20 carbon atoms, a substituted or unsubstituted, saturated or unsaturated cycloalkylene radical having from 3 to 20 carbon atoms, a substituted or unsubstituted arylene radical having from 3 to 20 carbon atoms, an arylenealkylene radical having from 4 to 20 carbon atoms, a heterocyclic radical or any linear or branched sequence of two or more of the radicals mentioned, if desired linked via ether, thioether, ester amine or amide structures, X is a covalent bond to $R^2$ or O, S or $NR^3$, where $R^3$ is a hydrogen atom or a substituted or unsubstituted, linear or branched, saturated or unsaturated alkyl radical having from 1 to 20 carbon atoms, a substituted or unsubstituted, saturated or unsaturated cycloalkyl radical having from 3 to 20 carbon atoms, a substituted or unsubstituted aryl radical having from 3 to 20 carbon atoms, a heterocyclic radical or any linear or branched sequence of two or more of the radicals mentioned, Y is a hydrogen atom or a free functional group selected from the group consisting of hydroxyl, amino, amido, carbonyl, carboxyl, mercapto, sulfonyl, sulfinyl, sulfenyl, sulfate, nitro, nitrile, isonitrile, cyanate, silyl, silanyl, phosphine, phosphate, phosphite, phosphonate, acrylate, methacrylate, allyl, and vinyl and mixtures thereof and n is an integer from 1 to 20, with at least one isocyanate-reactive group of a compound having at least one isocyanate-reactive group, which group reacts with the OCN—$R^1$-moiety of the compound of the formula (1) wherein Y is retained as a hydrogen atom or a free functional group selected from the group consisting of hydroxyl, amino, amido, carbonyl, carboxyl, mercapto, sulfonyl, sulfinyl, sulfenyl, sulfate, nitro, nitrile, isonitrile, cyanate, silyl, silanyl, phosphine, phosphate, phosphite, phosphonate, acrylate, methacrylate, allyl, and vinyl and mixtures thereof or with at least one isocyanate-reactive group on a surface which has at least one isocyanate-reactive group, which group reacts with the OCN—$R^1$- moiety of the compound of the formula (1) wherein Y is retained as a hydrogen atom or a free functional group selected from the group consisting of hydroxyl, amino, amido, carbonyl, carboxyl, mercapto, sulfonyl, sulfinyl, sulfenyl, sulfate, nitro, nitrile, isonitrile, cyanate, silyl, silanyl, phosphine, phosphate, phosphite, phosphonate, acrylate, methacrylate, allyl, and vinyl and mixtures thereof.

2. A process as claimed in claim 1, wherein the compound which has at least one group which is reactive toward isocyanate is a monomer, polymer, dendrimer, hyperbranched polymer or star polymer containing at least one group which is reactive toward isocyanate.

3. A process as claimed in claim 1, wherein the surface which has at least one group which is reactive toward isocyanate is a surface of wood, glass, textiles, ceramic materials, leather, paper, plastic, stone, concrete, metals or metal alloys, with the proviso that these surfaces have at least one group which is reactive toward isocyanate.

4. A process as claimed in claim 1, wherein the group which is reactive toward isocyanate is selected from the group consisting of hydroxyl, amino, amido, carboxyl and mercapto and mixtures thereof.

5. A process as claimed in claim 2, wherein the group which is reactive toward isocyanate is selected from the group consisting of hydroxyl, amino, amido, carboxyl and mercapto.

* * * * *